(12) United States Patent
Trainoff et al.

(10) Patent No.: US 10,900,006 B2
(45) Date of Patent: Jan. 26, 2021

(54) METHOD AND APPARATUS TO MITIGATE EVAPORATION IN HIGH THROUGHPUT MEASUREMENTS

(71) Applicant: Wyatt Technology Corporation, Goleta, CA (US)

(72) Inventors: Steven P. Trainoff, Santa Barbara, CA (US); Shiva Ramini, Thousand Oaks, CA (US)

(73) Assignee: WYATT TECHNOLOGY CORPORATION, Goleta, CA (US)

( * ) Notice: Subject to any disclaimer, the term of this patent is extended or adjusted under 35 U.S.C. 154(b) by 0 days.

(21) Appl. No.: 16/854,852

(22) Filed: Apr. 21, 2020

(65) Prior Publication Data

US 2020/0248118 A1    Aug. 6, 2020

Related U.S. Application Data

(63) Continuation of application No. 16/384,970, filed on Apr. 16, 2019, now Pat. No. 10,626,359, which is a
(Continued)

(51) Int. Cl.
*G01N 15/06* (2006.01)
*C12M 1/32* (2006.01)
(Continued)

(52) U.S. Cl.
CPC .............. *C12M 23/12* (2013.01); *B01L 7/00* (2013.01); *B01L 9/523* (2013.01);
(Continued)

(58) Field of Classification Search
CPC .... G01N 30/74; G01N 21/00; G01N 21/6452; G01N 21/0332; G01N 21/253; G01N 35/0099; G01N 2030/025; G01N 2030/027; G01N 30/461; G01N 2035/00356; G01N 21/05; G01N 21/33; G01N 33/54366; G01N 15/0211; G01N 15/06; G01N 2015/0038; G01N 2015/0053; G01N 2015/0065; G01N 2015/0222; G01N 2015/0687; G01N 2015/0693; G01N 2015/1006; G01N 2021/0325; G01N 2035/00277; G01N 2035/00306; G01N 2035/00346; G01N 2035/0405; G01N 2201/0231; G01N 2201/12; G01N 30/7233; G01N 33/497;
(Continued)

(56) References Cited

U.S. PATENT DOCUMENTS 9,279,797 B2 *   3/2016  Clements .............. G01N 21/01
2004/0258563 A1 * 12/2004  Young ................ G01N 21/0303
                                                        422/400
(Continued)

*Primary Examiner* — Michael P Stafira
(74) *Attorney, Agent, or Firm* — Leonard T. Guzman

(57) ABSTRACT

A method and apparatus are disclosed for the collection of light scattered from a liquid sample contained within a multiwell plate for which evaporation from the wells is mitigated by the application of a barrier between the liquid sample and the environment. A vertical thermal gradient is applied across the vessel so that condensation is inhibited from forming on the interior surface of the barrier, thus permitting clear illumination of the sample for visual imaging, fluorescence studies and light scattering detection.

9 Claims, 3 Drawing Sheets

Related U.S. Application Data continuation of application No. 15/727,521, filed on Oct. 6, 2017, now Pat. No. 10,260,033.

(51) Int. Cl.
  *B01L 9/00* (2006.01)
  *G01N 35/02* (2006.01)
  *G01N 15/02* (2006.01)
  *B01L 7/00* (2006.01)
  *G01N 21/25* (2006.01)
  *G01N 21/00* (2006.01)
  *G01N 35/00* (2006.01)
  *G01N 15/00* (2006.01)

(52) U.S. Cl.
  CPC ......... *G01N 15/0211* (2013.01); *G01N 15/06* (2013.01); *G01N 21/00* (2013.01); *G01N 21/253* (2013.01); *G01N 35/028* (2013.01); *B01L 2200/142* (2013.01); *B01L 2300/041* (2013.01); *B01L 2300/046* (2013.01); *B01L 2300/0654* (2013.01); *B01L 2300/0829* (2013.01); *B01L 2300/1827* (2013.01); *B01L 2300/1872* (2013.01); *G01N 2015/0038* (2013.01); *G01N 2015/0053* (2013.01); *G01N 2015/0065* (2013.01); *G01N 2015/0222* (2013.01); *G01N 2015/0687* (2013.01); *G01N 2015/0693* (2013.01); *G01N 2035/00356* (2013.01)

(58) Field of Classification Search
  CPC .. G01N 35/00; G01N 35/028; G01N 35/1002; G01N 15/10; G01N 15/1434; G01N 15/1463; G01N 1/10; G01N 1/405; G01N 1/44; G01N 2021/335; G01N 2021/399; G01N 2021/6417; G01N 2021/6439; G01N 2021/6484; G01N 2030/128; G01N 2030/743; G01N 2035/00366; G01N 2035/00445; G01N 2035/1051; G01N 21/01; G01N 21/031; G01N 21/15; G01N 21/276; G01N 21/3504; G01N 21/39; G01N 21/6408; G01N 21/6486; G01N 21/76; G01N 2201/024; G01N 2201/0446; G01N 2201/0633; G01N 2496/80; G01N 2570/00; G01N 2800/347; G01N 30/06; G01N 30/12; G01N 30/14; G01N 30/34; G01N 30/7266; G01N 30/78; G01N 33/0027; G01N 33/487; G01N 33/6848; G01N 33/6851; G01N 35/04; G01N 7/02; G01N 15/00; G01N 15/02; G01N 15/0656; G01N 15/1404; G01N 15/1468; G01N 15/1475; G01N 1/14; G01N 1/22; G01N 1/2202; G01N 1/2205; G01N 1/2214; G01N 1/2226; G01N 1/28; G01N 1/30; G01N 1/42; G01N 2001/1037; G01N 2001/1454; G01N 2001/2223; G01N 2001/2229; G01N 2001/2238; G01N 2001/2282; G01N 2001/242; G01N 2001/302; G01N 2001/4027; G01N 2001/4033; G01N 2015/0046; G01N 2015/105; G01N 2015/1445; G01N 2015/1447; G01N 2015/1452; G01N 2015/1454; G01N 2015/1486; G01N 2015/1493; G01N 2015/1495; G01N 2015/1497; G01N 2021/151; G01N 2021/158; G01N 2021/1704; G01N 2021/3513; G01N 2021/3595; G01N 2021/6441; G01N 2021/6482; G01N 2021/8578; G01N 2030/062; G01N 2030/085; G01N 2030/121; G01N 2030/143; G01N 2030/3038; G01N 2033/4975; G01N 2035/00148; G01N 2035/00316; G01N 2035/00376; G01N 2035/00435; G01N 2035/0422; G01N 2035/0425; G01N 2035/0443; G01N 2035/0455; G01N 2035/0463; G01N 2035/0465; G01N 2035/1076; G01N 21/03; G01N 21/0303; G01N 21/09; G01N 21/274; G01N 21/31; G01N 21/61; G01N 21/6428; G01N 21/645; G01N 21/6458; G01N 21/763; G01N 21/85; G01N 2201/0221; G01N 2201/061; G01N 2201/0612; G01N 2201/0636; G01N 2203/0005; G01N 2203/0094; G01N 2203/0286; G01N 2458/15; G01N 2560/00; G01N 27/00; G01N 27/4146; G01N 27/62; G01N 30/02; G01N 30/08; G01N 30/20; G01N 30/24; G01N 30/30; G01N 30/6078; G01N 30/7206; G01N 33/0004; G01N 33/004; G01N 33/005; G01N 33/0057; G01N 33/1826; G01N 33/227; G01N 33/4836; G01N 33/49; G01N 33/4972; G01N 33/5008; G01N 33/5014; G01N 33/5041; G01N 33/52; G01N 33/574; G01N 33/6803; G01N 33/6863; G01N 33/82; G01N 35/00009; G01N 35/00029; G01N 35/00732; G01N 35/0098; G01N 35/026; G01N 35/10; G01N 35/1004; G01N 35/1009; G01N 35/1065; G01N 35/1072; G01N 35/1074; G01N 35/109; G01N 3/08; G01N 3/32; G01N 3/42; B01L 7/52; B01L 2300/0654; B01L 2300/0829; B01L 2300/1827; B01L 2300/1822; B01L 3/50273; B01L 2300/18; B01L 3/502715; B01L 3/50851; B01L 2300/041; B01L 2200/0647; B01L 2200/0689; B01L 2300/14; B01L 7/00; B01L 2200/026; B01L 2200/141; B01L 2200/142; B01L 2300/046; B01L 2400/0409; B01L 3/5023; B01L 3/50853; B01L 9/523; B01L 2200/025; B01L 2200/028; B01L 2200/10; B01L 2300/021; B01L 2300/06; B01L 2300/0819; B01L 2300/123; B01L 2300/1872; B01L 2300/1894; B01L 7/54; B01L 1/02; B01L 1/025; B01L 1/04; B01L 2200/023; B01L 2200/04; B01L 2200/12; B01L 2200/147; B01L 2200/16; B01L 2300/025; B01L 2300/044; B01L 2300/0627; B01L 2300/0636; B01L 2300/0672; B01L 2300/0877; B01L 2300/0887; B01L 2300/1805; B01L 2300/1844; B01L 2400/0481; B01L 2400/049; B01L 3/0275; B01L 3/502; B01L 3/502738; B01L 3/502761; B01L 2200/0605; B01L 2200/0673; B01L 2200/0684; B01L 2200/14; B01L 2200/143; B01L 2200/145; B01L 2200/148; B01L 2200/18; B01L 2300/024; B01L 2300/042; B01L 2300/049; B01L 2300/0609; B01L 2300/0663; B01L 2300/0812; B01L 2300/0838; B01L 2300/0848; B01L
2300/0851; B01L 2300/0858; B01L
2300/0883; B01L 2300/0893; B01L
2300/12; B01L 2300/1883; B01L
2400/0487; B01L 2400/0605; B01L
2400/0655; B01L 2400/0683; B01L
3/502707; B01L 3/508; B01L 3/5085;
B01L 3/50855; B01L 3/50857; B01L
7/525; B01L 7/5255; B01L 9/00; B01L
9/06; B01L 9/543

See application file for complete search history.

(56) References Cited

U.S. PATENT DOCUMENTS

| | | | | |
|---|---|---|---|---|
| 2005/0237528 | A1* | 10/2005 | Oldham | B01L 3/5027 |
| | | | | 356/414 |
| 2006/0024831 | A1* | 2/2006 | Kao | B01L 3/50851 |
| | | | | 356/243.1 |
| 2008/0003649 | A1* | 1/2008 | Maltezos | B01L 3/50851 |
| | | | | 435/91.2 |
| 2015/0111287 | A1* | 4/2015 | Rawle | B01L 7/52 |
| | | | | 435/287.2 |
| 2015/0362476 | A1* | 12/2015 | Clements | G01N 21/01 |
| | | | | 506/10 |

* cited by examiner

METHOD AND APPARATUS TO MITIGATE EVAPORATION IN HIGH THROUGHPUT MEASUREMENTS

PRIORITY

This application is a continuation of U.S. patent application Ser. No. 16/384,970, filed Apr. 16, 2019, which is a continuation of U.S. patent application Ser. No. 15/727,521, filed Oct. 6, 2017.

RELATED APPLICATIONS AND PATENTS

The following patents relate to the measurement of the physical properties of liquid samples in a multiwell plate and are hereby incorporated by reference:

U.S. Pat. No. 6,519,032 B1, S. C. Kuebler and J. Bennett, "Fiber optic apparatus and use thereof in combinatorial material science," issued Feb. 11, 2003.

U.S. Pat. No. 6,819,420 B2, S. C. Kuebler and J. Bennett, "Fiber optic apparatus and use thereof in combinatorial material science," issued Nov. 16, 2004.

U.S. Pat. No. 8,964,177 B2, D. I. Some, M. I. Larkin, P. G. Neilson, and D. N. Villalpando, "Method and apparatus to illuminate sample and containing vessel in a light scattering detector," issued Feb. 24, 2015.

U.S. Pat. No. 8,976,353 B2, M. I. Larkin, A. D. Hanlon, D. I. Some, R. J. Sleiman, D. N. Villalpando, "Mutiwell plate lid for improved optical measurements," issued Mar. 10, 2015.

U.S. Pat. No. 9,347,869 B2, M. I. Larkin, A. D. Hanlon, D. I. Some, R. J. Sleiman, D. N. Villalpando, "Mutiwell plate lid for improved optical measurements," issued May 24, 2016.

U.S. Pat. No. 9,658,156 B2, A. D. Hanlon, M. I. Larkin, "Method of characterizing interactions and screening for effectors," issued May 23, 2016.

U.S. Pat. No. 9,459,207 B2, A. D. Hanlon, M. I. Larkin, "Method of characterizing interactions and screening for effectors," issued Oct. 4, 2016.

BACKGROUND

Throughout this specification, the term "particle" refers to the constituents of liquid sample aliquots that may be molecules of varying types and sizes, nanoparticles, virus like particles, liposomes, emulsions, bacteria, colloids, etc. Their size range may lie between 1nm and several thousand micrometers.

Light scattering is a non-invasive technique for characterizing macromolecules and a wide range of particles in solution. The two types of light scattering detection frequently used for the characterization of macromolecules are static light scattering (SLS) and dynamic light scattering (DLS).

Static light scattering experiments involve the measurement of the absolute intensity of the light scattered from a sample. This measurement allows the determination of the size of the sample molecules, and, when coupled with knowledge of the sample concentration, allows for the determination their weight average molar mass. In addition, nonlinearity of the intensity of scattered light as a function of sample concentration may be used to measure interparticle interactions and associations.

Dynamic light scattering is also known as quasi-elastic light scattering (QELS) and photon correlation spectroscopy (PCS). In a DLS experiment, time-dependent fluctuations in the scattered light signal are measured using a fast photodetector. DLS measurements determine the diffusion coefficient of the molecules or particles, which can in turn be used to calculate their hydrodynamic radius.

Extensive literature has been published describing methods for making both static and dynamic light scattering measurements in flowing and batch (non-flowing) systems. See, for example, P. J. Wyatt, "Light scattering and the absolute characterization of macromolecules," Analytica chimica Acta, 272, 1-40, (1993). Many commercially available instruments allow for the measurement of SLS and/or DLS, and there are many methods to perform these measurements. For example, U.S. Pat. No.: 6,819,420, by Kuebler and Bennet, discloses a method and apparatus for measuring the light scattering properties of a solution in a vessel wherein light may be transmitted into the solution through the bottom of the optically transparent vessel, and the scattered light may be detected through the same surface by means of an optical fiber coupled with a photodiode.

With the development and improvement in the optical quality of multiwell plates, it has become possible to make both SLS and DLS, as well as other measurements of the physical properties, such as fluorescence, concentration, and absorption, directly from samples contained therein. Methods capable of measuring samples directly in these multiwell plates are generally desirable given both the high-throughput nature of the measurements and the reduced sample volume requirements. Multiwell plates may contain any number of independent wells. Most commercially available plates for analyses such as these contain either 96, 384, or 1536, each well is able to contain a different sample, and all wells may be tested in a single data collection run. In addition, use of these plates obviates the laborious need to clean and dry individual scintillation vials after each measurement. These plates generally have very low volume wells, and commercially available multiwell plate based measurement instruments are capable of light scattering measurements from sample volumes of 4 μL or less. These tiny sample volumes are of great benefit when one has a limited amount of sample from which to make measurements, particularly when compared to the 300 μL or larger sized measurement volumes often required by other light scattering techniques.

All light scattering measurements are subject to various sources of unwanted noise, which can lead to inaccurate measurements of the light scattering properties of the sample itself. This noise may be due to unknown contaminants present in the sample, soiled or improperly manufactured or maintained or dirty surfaces of the vessel through which the light transmitted and/or measured passes. Imperfections in the surfaces of the vessel or other contaminants contained therein or adhered thereto, such as bubbles, precipitated particles, residue, etc., may also cause background scattering which can also interfere with proper measurements of scattered light from the sample or may interfere with the beam or scattered light expected to exit the vessel and be measured by a detector. In other words, deleterious high background signal, or noise, is caused by light scattered from anything other than the sample. This background noise decreases the light scattering instrument's sensitivity due to the increase in the noise present in relation to the useful signal scattered from the sample itself, and therefore an overall reduction in the signal-to-noise ratio upon which the sensitivity of the measurement is dependent. For DLS measurements, higher sample concentrations of precious sample materials are required to overcome this background signal.

While light scattering detection in multiwell plates has many advantages, including high throughput measurements, the ability to control the temperature of multiple samples simultaneously, and the ability to monitor aggregation and other self and hetero associations, to name only a few, there are special pitfalls associated with these measurements. For example, gas bubbles may adhere to the bottom or side of the well, or may float within the sample itself or at or near the fluid meniscus. In addition, multiwell plates may be reused, and thus careful cleaning is required between sample collections; imperfect washing may leave behind artifacts or residues that can deleteriously affect light scattering measurements. The amount of time required of an operator or a robotic injector to fill an entire plate opens up the possibility for dust particles to fall into the wells or other contaminants to be introduced thereto by the handling of the plates while loading wells, such as oil from skin, powder from handling gloves, cosmetics, flaking skin cells, debris from loading pipettes. In order to mitigate problems associated with evaporation, an oil overlay is often used to "cap" a well, and residues and/or droplets from this oil may remain in a well. In order to identify potentially contaminated sample cell wells, Some, et.al. disclosed, in U.S. Pat. No. 8,964,177 B2, a system whereby the multiwell plate is illuminated enabling high resolution photos of wells to be taken and stored in software without interfering with light scattering measurements, and thus, when analyzing the data, correlations can be made between data and cleanliness of the well from which it was taken. While not eliminating the contaminants, this system helps to alleviate some of the errors associated with light scattering measurements in multiwell plates.

Another problem associated with all so-called "batch" light scattering measurements, that is, measurements taken from a static sample within a flow cell, wherein, generally, the sample is exposed at least partially to the environment via a sample/air interface, is the issue of evaporation. Evaporation can alter the sample state, skew results through altered background intensity, or prohibit light scattering measurement entirely. Partial evaporation of the solvent from a well increases the concentration of the dissolved solute, which may have deleterious effects on the sample itself. Evaporation can also impact the meniscus as well as meniscus height in the well, leading to inconsistent results. More substantial evaporation of the sample solvent can often completely prevent accurate measurement, which is a problem particularly prevalent in very small volume multiwell plates where even a small amount of evaporation results in a large change in the height of the fluid level. Even for the larger sample volumes contained in 96 well plates, evaporation concerns often prevent useful extended measurement times as well as measurements at elevated temperature, making studies of temperature dependence exceedingly difficult.

Traditionally evaporation from well plates has been addressed by either a film or cover placed on the surface of the plate above the sample wells or, as mentioned above, a layer of oil overlaying the sample contained in each well. However, for light scattering measurements, both of these commonly used evaporation mitigation techniques can be problematic. Films and solid transparent covers can promote significant backscatter from the interface of the exiting light beam with the lid or film. While this problem may be partially overcome by employing a lid that absorbs light at the wavelength of the illumination source, other problems still exist. One of the largest problems associated with evaporation in covered multiwell plates concerns fluid contained in the wells evaporating and then condensing on the inner surface of the film or cover. This layer of condensation is highly scattering and is generally non-uniform from well to well, and thus again, the backscatter intensity may overwhelm sample signal, greatly decreasing the sensitivity of the measurement, and often leading to erroneous results. While the use of an oil overlay eliminates the issue of condensation, the potentially negative interactions of oil and sample molecules are well known, as documented in the 2004 article by L. S. Jones et al, "Silicone oil induced aggregation of proteins," published in the Journal of Pharmaceutical Sciences, v. 94, pages 918-927. Such unintended interactions may result in an inaccurate representation of the true sample characteristics, and may occur without the knowledge of the experimenter. In addition, oil overlays can be difficult and time consuming to apply to each sample containing well. The practical requirement of such an oil overlay to control condensation prevents many users from attempting multiwell plate-based light scattering measurements.

Many of these issues were discussed and addressed in U.S. Pat. No. 8,976,353 B2 by Hanlon, et.al. with the use of a novel lid structure which contained posts or tubes which protruded from the bottom lid surface into each well of the sample. These lids sealed each well individually as well as provided means to direct or collect the illuminating beam after passage through the sample. However, the expense of these specialized lid elements in addition to difficulties with cleaning between uses may prevent some researchers from employing them. Further, these specialized lid elements tend to interfere with onboard optical cameras such as those discussed above and in U.S. Pat. No. 8,964,177 B2, which image the contents of the wells.

It is an objective of the present invention to offer a simple, user friendly means to mitigate many of the problems associated with evaporation from samples in multiwell plates without the need for oil overlays, which can be burdensome and may interact with samples under investigation, as well as offering a cost effective alternative to utilizing specialized multiwell plate lids. Another objective of the present invention is to provide evaporation mitigation means while retaining the ability to take high quality photographs of the wells of a multiwell plate contained within a light scattering instrument.

A BRIEF DESCRIPTION OF THE SEVERAL VIEWS OF THE DRAWINGS

FIG. 1 shows a light scattering/photographic multiwell plate reader as described by in U.S. Pat. No. 8,964,177 B2 incorporating a means to provide illumination for photographs.

A DETAILED DESCRIPTION OF THE INVENTION

Figure 1:
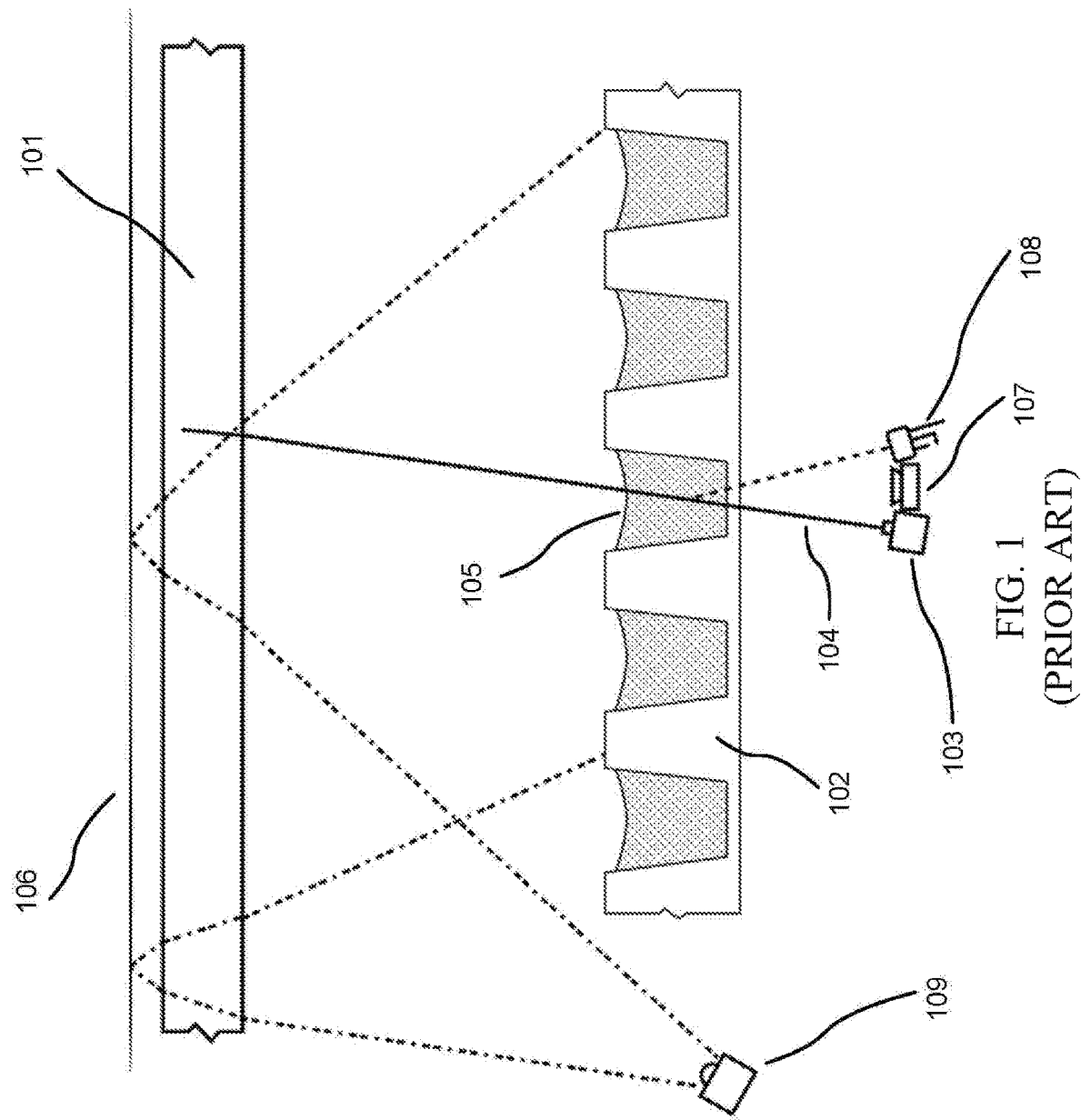

Another common use for multiwell plates where evaporation can be a concern is in the biochemical field of polymerase chain reaction (PCR) experiments. In a typical PCR experiment, the reaction of a liquid sample of proteins, for example, are exposed to varying amounts of a particular enzyme placed within individual conical vials, each with its own incorporated lid, and these vials are placed within a single plate placed within the walls of a multiwell plate, generally adapted to receive the conical vials. The properly loaded multiwell plate then undergoes thermal cycling, generally by being placed within a chamber that cycles between approximately 96° C. for the denaturation step and down to approximately 60° C. for the annealing step. This cycling is generally repeated between 20 and 40 times. As with light scattering applications, evaporation can be a problem in PCR analysis. Means by which the PCR samples are heated and cooled can vary depending on the instrumentation. In some cases, the vials or strips of vials are contained within a heat conducting plate, which is used to raise and lower the temperature. In these cases a top plate is often placed into contact with the lids of the vials. Throughout the cycling procedure there is a risk of evaporation from the sample, resulting in condensation of the solvent upon the inner lid of each vial. This evaporation necessarily changes the concentration remaining sample concentration contained within the main body of the vial, and over the entire cycling process, these variations in sample can affect results. Further, some of the techniques used to heat the chamber, for example, external heaters, can result in uneven heating throughout the chamber, expansion of the retaining plate, and uneven evaporation across the samples contained therein, thus some vials may experience evaporation induced concentration change, while others may have more significant changes, and thus uniformity of results are not guaranteed. In addition, as the plates are heated by a thermal block within the retaining bottom plate and a heated lid located just above and/or in contact with the sample lids, the wells can expand and introduce small spaces between the well walls and the cap/sealing means where gasses can escape. These expansion issues are partially mitigated by two-piece construction plates such as the Framestar™ plates by 4titude® (Wotton, Surrey, UK) that utilize polypropylene tubes and polycarbonate holding frames, though even these advanced systems still result in some lost sample volume by evaporation.

While evaporation concerns pose challenges to both PCR and light scattering detection, it should be noted that PCR is primarily a preparative technique, and thus the methods for dealing with evaporation in PCR can differ from methods utilized with light scattering measurements. For example Yamamoto, et.al., in European Patent Publication No. 0 311 440 B1, disclose a multi-step, small footprint, preparatory instrument for dispensing, preparing and cycling samples for subsequent analysis by another instrument. In one region of the apparatus an automated pipette takes sample from reagent bottles placed on one stage and injects them into prepared wells of a multiwell plate on a second stage. The stage containing the multiwell plate is then moved, by an automated system, into the heating chamber, isolated from the preparative chamber, where the samples are brought to the desired temperature by placing a heating block in contact with the multiwell plate both above and below. In one embodiment of the Yamamato invention, when the desired temperature has been reached (and cycles through temperatures achieved as necessary), the bottom heating plate may be removed from the sample, while retaining the top heating in heat transmitting contact with the multiwell plate. This method encourages the cooling rate of the liquid samples in the wells of the multiwell plate to be more rapid than the cooling rate of the upper heater, and therefore liquid vaporized in the space in the well can be cooled discouraging the condensation of sample on the lower surface of the upper heater plate. Once the multiwell plate is at an appropriate temperature, the upper heating plate is removed from contact with the multiwell plate, which is then moved back into the loading chamber, and either removed manually from the instrument or further processed by the addition of other compounds, enzymes, etc., prior to being returned to the heating chamber for further temperature cycling. Once the sample preparation is complete, the multiwell plate can be moved from the PCR station to an analysis instrument which can be either one which removes the prepared samples from the wells for analysis, for example, by injection into an chromatography system, or they may be analyzed within the plate itself by any number of means, including light scattering.

However, even with these advanced, automated preparatory systems, evaporation still remains a problem when it comes to the direct in-situ analysis of the samples within the wells of the multiwell plate. While the device of Yamamoto may succeed in retaining as much of the sample within the well as possible during preparation, there is still ample time within the actual analysis instrument for evaporation to be a concern. As discussed above, instruments such as the DynaPro Plate Reader II (Wyatt Technology, Santa Barbara, Calif.), enable the measurement of light scattered from samples contained within multiwell plates, however, light scattering measurement, particularly DLS measurements, generally take 5-10 seconds per measurement. Therefore in order to scan a complete 1536 well plate could take several hours. During this time, it is generally important that all the wells maintain as close to their original state as possible, and any evaporation occurring between the time the measurements of the first and last sample will result in inaccuracies in the derived results due to the physical and chemical changes of the sample containing well. Therefore, it is of critical importance that the effects of evaporation be mitigated to the largest extent possible when performing light scattering measurements, whether or not the samples have previously undergone PCR processing.

As discussed above, a common method for discouraging evaporation from individual wells is to provide a physical barrier covering the top of each well. These methods can include specialized lids, an oil overlay or an adhesive barrier such as tape adhered to the top of the well plate. It is an objective of the present invention to enable both the photographic imaging of the well itself and light scattering detection of the sample while also mitigating evaporation within the multiwell plate and, in particular, condensation on any barrier placed on the plate. The prior art, including that discussed above, is incompatible with these goals. For example the lids proposed by Hanlon, beyond being expensive, will interfere with photography of the wells. The heating plates in contact with the multiwell plate discussed by Yamamoto, as well as those utilized in the Framestar system, will block both illumination of the plate for photographic purposes as well light scattering detection via a moveable probe (or moving plate relative to a fixed probe or a combination thereof).

Several embodiments of the present invention utilize both an active, though optically compatible, barrier system coupled with a more passive heating system, permitting optical access to the plate for both light scattering and photographic probes while preventing both evaporation and interfering condensation. FIG. 1 shows a conventional light scattering/photographic multiwell plate, such as described by Some in U.S. Pat. No. 8,964,177 B2 which utilizes an absorbing/transmitting optical structure 101 located above the wells of a multiwell plate 102. This absorbing/transmitting optical structure 101, absorbs light at the wavelength of the light scattering illumination source 103 generally a laser, but transmits light at other wavelengths. This light scattering illumination source 103 generates a beam 104 at a wavelength of $\lambda_1$. The light scattering source beam 104 passes through the bottom of a multiwell plate 102. The light scattering beam emerges from the sample contained within an individual well 105, and is intercepted by absorbing/transmitting optical structure 101 located above the multiwell vessel. Light scattered from the illuminating beam 104 by the sample contained in the well 105 is detected by one or more light scattering detectors 108, wherein this optical structure 101 has been selected to absorb radiation at the wavelength of the light scattering source. A second image illumination source 109 emits a generally more diffuse beam at a different wavelength, $\lambda_2$, or range of wavelengths, and its beam is incident at an angle on the absorbing/transmitting optical structure 101, generally made of a special glass, which is located above the multiwell plate 102. This absorbing/transmitting optical structure absorbs light at the wavelength of the laser, $\lambda_1$, but transmits at least some of the light at the wavelength, $\lambda_2$, of the image illumination source 109. Optical filter glass that absorbs at particular wavelengths that may be employed as the absorbing/transmitting optical structure 101 is available from optical suppliers such as Schott North America, Inc. (Elmsford, N.Y.). The transmitted light from the imaging illumination source is then scattered and reflected from a diffusing surface 106, which can take many forms including that of a plain piece of white paper, and after transmission back through the absorbing/transmitting optical structure 101, illuminates the wells from above. The absorbing/transmitting optical structure 101 therefore acts as a "beam dump" for the light scattering source 103 while transmitting light required for illumination at a wavelength, which the camera 107 is able to register. It should also be noted that the image illumination source 104 or an additional diffuse illumination source may act as an excitation radiation source to induce fluorescence in one or more samples contained within the wells of the plate 102. In this case a fluorescence detector, such as a independent fluorescence probe comprising, for example, a photodiode and a means to filter light at the wavelength $\lambda_2$. In another embodiment the camera, coupled with an appropriate filter, or a second camera and filter may act as the fluorescence detector. In other embodiments, multiple probes may be utilized to measure both static and dynamic light scattering as well as fluorescence as presented in pending U.S. patent application Ser. No. 15/583,899,"High throughput method and apparatus for measuring multiple optical properties of a liquid sample," filed May 1, 2017 by Hsieh, et.al, incorporated herein by reference. Some embodiments of the present invention include independent probes for the measurement of fluorescence and light scattering, but in some embodiments, the fluorescence excitation source may be a diffuse source such as the image illumination source 104 as discussed above.

The absorbance and transmittance of the plate 101 may be chosen to correspond to the wavelengths of the two light sources, or vice versa, and some variation of wavelengths $\lambda_1$ and $\lambda_2$ may be possible. For example, a plate may be chosen which absorbs at 830 nm±30 nm, but transmits at all other wavelengths. Therefore the wavelength of the laser may operate anywhere within that range or on the peripheries thereof so long as the plate adequately absorbs the beam such that light scattering signals are not deleteriously affected and the instrument is not damaged.

While a plain sheet of white paper may act as a diffusing surface 106, it is also possible to use any number of other surfaces, such as a diffusing plastic produced by 3M (St. Paul, Minn.), so long as they aid in the diffusion of light to be transmitted back through the absorbing plate 101. A thin weatherproof vinyl sheet has also proven very useful as a diffusing element 106. One particular advantage of this specific element is that the weatherproofing aids in maintaining the integrity of the diffusing sheet over many temperature ramping cycles, which may be common in high throughput light scattering experiments, for example. Further the diffusing surface need not even be an additional element, but rather could be a special diffusing surface incorporated into the glass or a diffusing layer etched, adhered, or placed thereon.

While the systems discussed thus far represent an improvement on the prior art, they do not yet solve the fundamental challenge at issue in this disclosure, control of evaporation without interfering with optical access to the each well and without the deleterious effects of oil capping each well. For most applications the use of a barrier such as transparent adhesive tape covering the mouths of the wells or a lid is acceptable, but this raises the problem of condensation on the tape unacceptably increases the background scattering from the probe laser. The essential inventive element is to insure that each well sees a vertical temperature gradient, with the top of each well, held at a higher temperature than the bottom of the well. This prevents droplets from forming on the sealing tape. It also has the side benefit of preventing convection within the fluid of each well.

There are several ways that the vertical temperature gradient can be applied. The simplest is to add a heating element to the top of the instrument that heats the air above the plate. Indeed, when the instrument is run above ambient temperature, the measurement chamber is insulated from the environment but regardless of how efficient is the insulation heat will be lost through these surfaces. If the instrument is heated from below, which is often the case, the upper surface of the measurement chamber is naturally cooler than the interior, which generates a small negative temperature gradient, which exacerbates the condensation problem. Adding the top heater allows the instrument to overwhelm the heat lost to the environment to generate the desirable positive temperature gradient.

An alternative method of applying a gradient, rather than heating the air at the top of the measurement chamber is to use one or more IR illuminators to apply infrared radiation to the sealing tape. Since the tape has a small thermal mass, it can be heated rapidly, without substantially affecting the temperature of the samples within each well. Moreover, if the camera, DLS, SLS, or florescence sensors are sensitive to infrared illumination used to create the thermal gradient, the illuminator operation can be multiplexed with the measurement sensors so that they only apply light when the wells are not actively being measured.

Figure 2:
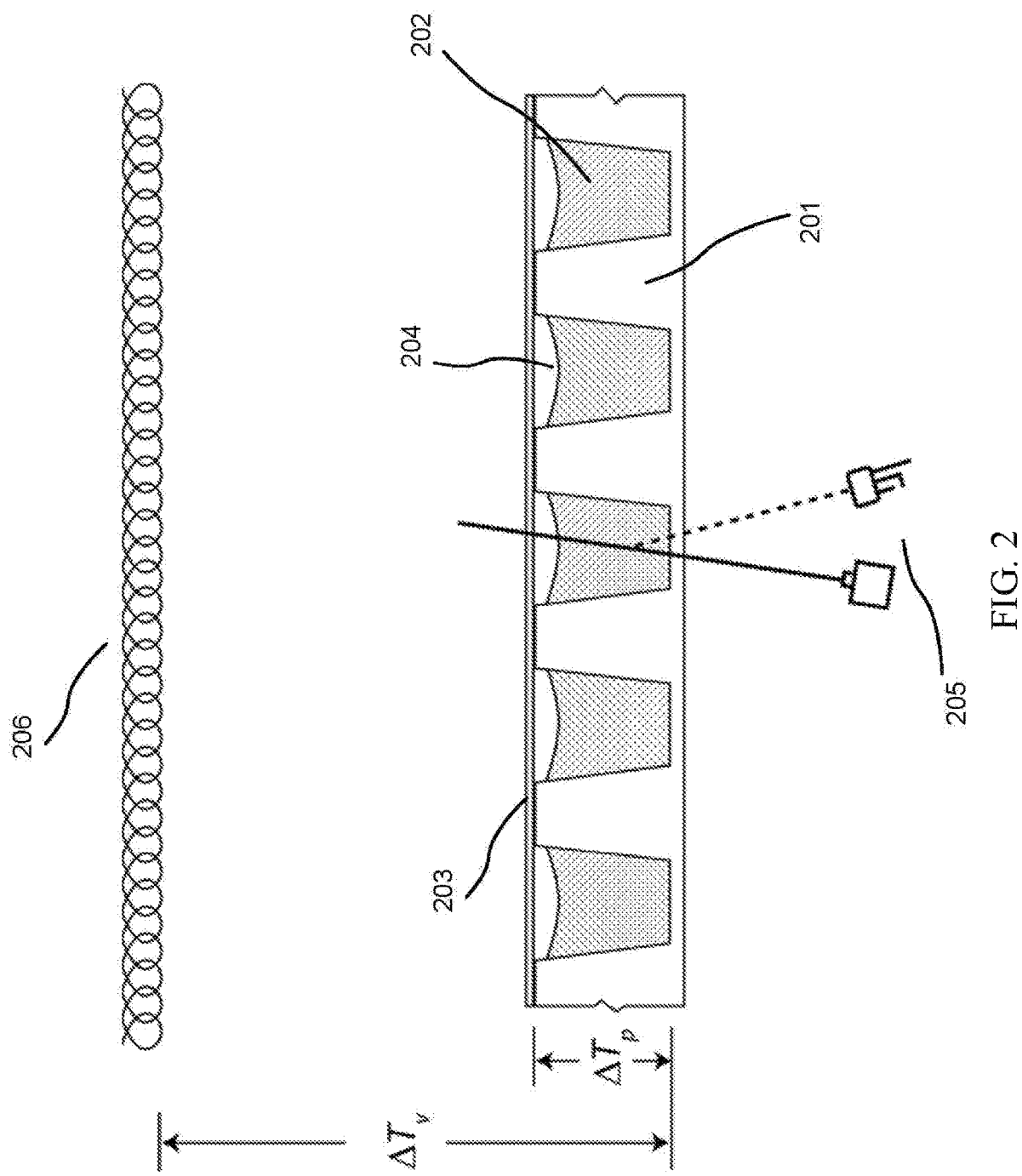
FIG. 2 illustrates critical elements of an embodiment of the invention including a heating source to generate a temperature gradient across the collection enclosure as well as across the sample plate itself.

FIG. 2 illustrates the fundamental elements of the invention in one of its simplest forms. The multiwell plate 201 containing liquid samples 202 to be investigated. A barrier 203 such as transparent adhesive tape is placed on the top surface of the multiwell plate 202. A vapor region 204 of each well is defined as the space above the meniscus of the liquid sample 202 and the bottom of sealing barrier 203, in other words, the vapor region is the volume of each well not occupied by liquid sample. Beneath the multiwell plate 201 are placed the various optical investigation probes 205, which may include an optical camera, DLS and SLS detectors and related optics, as well as fluorescence detectors. In other embodiments, the probes located beneath the plate may be ends of optical fibers and associated optics as required that direct illumination to the sample or plate and/or collect and direct light from the sample and/or plate to the detection means. Above the sealed multiwell plate, but not in contact therewith, is a heating element 206. The purpose of the heating element is to generate a temperature gradient across the vertical height of the multiwell plate. However, it should be noted the measurement chamber is thermostated with either a heater or a Peltier device to a constant temperature and an additional static temperature gradient is introduced by the top heating element. In the preferred embodiment, this is achieved with a heater on the top surface, although it is clear that a vertical thermal gradient can also be achieved by placing an additional cooling element beneath the plate. However this variation is more difficult to achieve in practice as the light measurement activity beneath the plate interferes with generating a uniform cooling distribution.

The desired temperature gradient across the plate $\Delta T_p$ is that difference in temperature required to keep solvent from the sample in the gaseous state contained within the vapor region 204 of each cell in the gaseous state, that is to say that the temperature at the barrier $T_b$ is greater than the temperature of the liquid sample $T_s$, thus the gradient $\Delta T_p = T_b - T_s > 0$. For most aqueous samples in standard multiwell plates, $\Delta T_p$ will be approximately 0.5° C. This required temperature gradient may vary depending on the amount of sample in the wells, the types of sample, the solvent, the solute, the size of the wells, and other variables, however for each different sample configuration, the required $\Delta T_p$ can be determined and applied with the present invention. In order to achieve the required $\Delta T_p$, a significantly larger temperature gradient must be applied over the vertical height of the cavity, $\Delta T_v$, with the heating element located centimeters above the sample containing multiwell plate. So, for example, in one preferred embodiment of the invention shown in FIG. 3, the temperature gradient across the vertical height of the well plate containing chamber $\Delta T_v$ is roughly 30° C. in order to achieve the critical $\Delta T_p$ value of 0.5° C.

Figure 3:
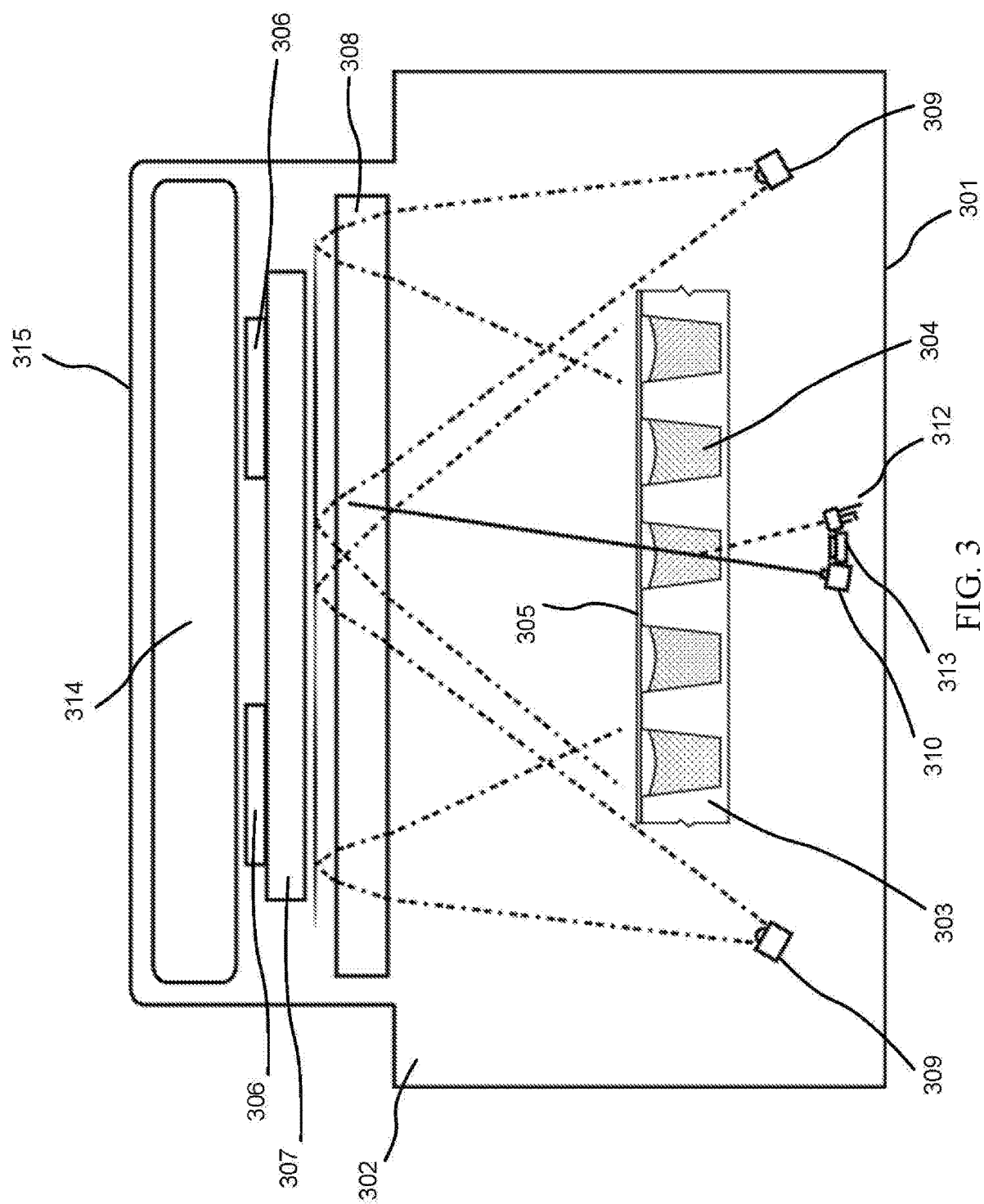
FIG. 3 shows a preferred embodiment of the invention with elements to mitigate evaporation and condensation while enabling collection of photographic and light scattering data from the sample wells.

FIG. 3 shows one preferred embodiment of the invention combining many elements so as to maximize the amount of information about samples analyzed by the plate reader. This particular novel embodiment permits measurement of several properties of the liquid samples while minimizing any negative issues associated with evaporation, which has heretofore not been possible. The plate reader instrument 301 houses a measurement chamber 302 into which is placed the filled multiwell plate 303. One or more of the wells of the multiwell plate contains a liquid sample 304. Samples to be protected against evaporation are covered with a transparent optical barrier 305. This barrier can take many forms such as an adhesive film or tape or a lid capable of sealing each well individually. Under certain, specialized circumstances, such as when all samples are of identical composition, a more general lid will suffice as a barrier, that is to say one wherein the wells share a vapor region, but the lid retains vapor from exiting the shared vapor region into the measurement chamber 302. The barrier, however, as previously stated, must separate vapor regions associated with the multiwell plate from that associated with the sample chamber, preventing, thereby, the evaporation of sample solvent into the measurement chamber. In addition the multiwell plate must be transparent to at least certain wavelengths of light discussed below, and in most cases will be transparent to all wavelengths of visible and UV light. The measurement chamber is sealed, generally from above, by a door element 315. Housed within this door element, or moved into place between the door and the plate when the door is closed, is one or more heating elements 306. These heating elements may independently provide uniform heat distribution across a given region or a heat distributor, such as a metal block 307 may be connected thereto to effective and efficiently distribute the heat applied by the heating elements 306. In order to permit the collection of photographic data, as discussed above, the plate 303 is preferably illuminated relatively uniformly. An absorbing/transmitting optical element 308 that absorbs light at certain wavelengths and transmits at others is positioned beneath the heat distributor 307. Optical filter glass which absorbs at particular wavelengths and which may be employed as the absorbing/transmitting optical structure are available from optical suppliers such as Schott North America, Inc. (Elmsford, N.Y.). One or more diffuse illumination sources 309 are positioned within the measurement chamber and directed to strike the absorbing/transmitting optical element. The optical properties of the absorbing/transmitting element are selected such that it transmits light at one or more of the wavelengths emitted by the diffuse illumination sources 309, but absorbs light at the wavelength of the light scattering source 310 discussed below. In a preferred embodiment light from the diffuse illumination source passes through the absorbing/transmitting element and is scattered from a diffusing surface 311, such as a plain piece of white paper. The light scattered by this diffusing surface is transmitted back through the absorbing/transmitting element 308 and illuminates the wells from above.

Positioned beneath the multiwell plate are one or more detector elements and accompanied illumination elements. In particular embodiments, a light scattering source 310 with a wavelength selected in the absorbing range of the absorbing/transmitting element 308 illuminates the sample 304 contained within a given well of the multiwell plate. The beam, emerging from the sample ultimately intersects the absorbing/transmitting element and is absorbed thereby. One or more light scattering detectors 312 collect light scattered by the illuminated sample. A camera element 313, also generally located beneath the well plate and that may be on the same movable stage as the light scattering illumination and detection means, takes photographic data of the plate and sample when the plate is illuminated by the diffuse illumination sources 309. Other detectors and illumination sources, for example ultraviolet (UV) light sources and fluorimeters may accompany the light scattering detector and illumination means beneath the multiwell plate. Further, it may be advantageous under certain circumstances to have the diffuse illumination sources themselves operate at multiple wavelengths or be accompanied by other diffuse illumination sources whereby diffuse illumination generated by these sources both enable photographic data to be collected by the camera element 313 as well as provide ultraviolet, excitation illumination to fluorescing samples. Variable wavelength photodiodes may be utilized or a plurality of diffuse light sources including those in the visible and in the UV spectrum may be utilized.

As discussed previously, in order for a temperature gradient of adequate magnitude to be applied across the height of the multiwell plate, generally of approximately 0.5° C., a much larger temperature gradient is required over the height of the measurement chamber 302. In some preferred embodiments this gradient must be approximately 30° C. In order to efficiently provide this temperature gradient without excessive loss of heat to the environment outside of the plate reader instrument itself, it is generally important to provide adequate thermal insulation.

Accordingly in insulation element 314 may be placed above the heating elements 306 in the lid element 315, thereby conserving the heat generated by the elements and reducing the amount of heat loss into the environment. Aerogels are an ideal insulator for this purpose as it is has a low density and low thermal conductivity, and they may be custom formed. In addition to heat escaping from above the heating elements, the entire measurement chamber should be appropriately insulated and vented such that the vertical gradient across the measurement chamber may be maintained. With this gradient maintained once the vapor pressure in the vapor region of the sealed well equilibrates as long as the necessary thermal gradient is maintained, evaporation from the sample is eliminated and condensation on the sealing film is prevented, permitting photographic as well as light scattering and other optical measurements heretofore not possible.

There are many embodiments of our invention that will be obvious to those skilled in the arts of measurement optics and fluid dynamics that are but simple variations of our basic invention herein disclosed that do not depart from the fundamental elements that we have listed for their practice; all such variations are but obvious implementations of the invention described hereinbefore and are included by reference to our claims, which follow.

What is claimed is:

1. An apparatus comprising:
  a barrier configured to be positioned above at least one well,
    wherein the at least one well is configured to contain a liquid sample,
    wherein a vessel comprises the at least on well,
    wherein the vessel is transparent and is configured to be placed within a measurement chamber,
    wherein a light measurement apparatus comprises the measurement chamber,
    wherein the light measurement apparatus is configured to measure light scattered from the liquid sample and to collect the light scattered from the liquid sample from below the vessel,
    wherein the barrier is configured to seal the at least one well from the measurement chamber;
  an insulating element positioned on an upper surface of the measurement chamber; and
  at least one heater positioned below the insulating element and above the barrier,
    wherein the at least one heater is configured to create a temperature gradient between the sample and an internal surface of the barrier to prevent formation of condensation on the internal surface,
    wherein the insulating element is configured to conserve heat generated by the at least one heater.

2. The apparatus of claim 1 wherein the barrier is adhesive tape.

3. The apparatus of claim 1 wherein the barrier is a transparent lid.

4. The apparatus of claim 1 wherein the at least one heater is an infrared illuminator.

5. The apparatus of claim 4 wherein the infrared illuminator is a flash lamp.

6. The apparatus of claim 1 wherein the vessel is a multiwell plate.

7. The apparatus of claim 1 wherein the temperature gradient is greater than 0.5° C.

8. A method comprising:
  positioning a barrier above at least one well,
    wherein the at least one well is configured to contain a liquid sample,
    wherein a vessel comprises the at least on well,
    wherein the vessel is transparent and is configured to be placed within a measurement chamber,
    wherein a light measurement apparatus comprises the measurement chamber,
    wherein the light measurement apparatus is configured to measure light scattered from the liquid sample and to collect the light scattered from the liquid sample from below the vessel,
    wherein the barrier is configured to seal the at least one well from the measurement chamber;
  positioning an insulating element on an upper surface of the measurement chamber; and
  positioning at least one heater below the insulating element and above the barrier,
    wherein the at least one heater is configured to create a temperature gradient between the sample and an internal surface of the barrier to prevent formation of condensation on the internal surface,
    wherein the insulating element is configured to conserve heat generated by the at least one heater.

9. The method of claim 8 wherein the vessel is a multiwell plate.

* * * * *